US00PP29643P3

(12) United States Plant Patent
O'Connell

(10) Patent No.: US PP29,643 P3
(45) Date of Patent: Sep. 4, 2018

(54) ***SEDEVERIA* X *ECHEVERIA* HYBRID PLANT NAMED 'LILAC MIST'**

(50) Latin Name: ***Sedeveria* x *Echeveria* hybrid**
Varietal Denomination: Lilac Mist

(71) Applicant: Renee O'Connell, Escondido, CA (US)

(72) Inventor: Renee O'Connell, Escondido, CA (US)

(73) Assignee: Altman Specialty Plants, Inc., Vista, CA (US)

( * ) Notice: Subject to any disclaimer, the term of this patent is extended or adjusted under 35 U.S.C. 154(b) by 0 days.

(21) Appl. No.: 15/330,623

(22) Filed: Oct. 18, 2016

(65) Prior Publication Data

US 2018/0110168 P1 Apr. 19, 2018

(51) Int. Cl.
*A01H 5/12* (2018.01)

(52) U.S. Cl.
USPC ..... Plt./373
CPC ..... *A01H 5/12* (2013.01)

(58) Field of Classification Search
USPC ..... Plt./373
See application file for complete search history.

*Primary Examiner* — Susan McCormick Ewoldt
(74) *Attorney, Agent, or Firm* — Cassandra Bright

(57) ABSTRACT

A new and distinct *Sedeveria* cultivar named 'Lilac Mist' is disclosed, characterized by a compact and chunky morphology which can fill a 9 cm pot with a single vegetative cutting. Grey-green foliage with distinctive violet blush. Suitability for combining with other ornamental plants. The new variety would typically be useful as container a plant or as landscape plants.

2 Drawing Sheets

Latin name of the genus and species: *Sedeveria* x *Echeveria* hybrid.

Variety denomination: 'LILAC MIST'.

BACKGROUND OF THE INVENTION

The new cultivar, *Sedeveria* 'Lilac Mist', is the product of a planned breeding program. The new variety originated from a cross pollination of the proprietary, unpatented, seed parent, *Sedeveria* 'Sed 09' with the pollen parent, an unpatented, proprietary variety of *Echeveria* referred to as 'Lei 12'. The cross pollination was made during February 2012 in Vista, Calif., at a commercial greenhouse. The new cultivar 'Lilac Mist' was discovered by the inventor, Renee O'Connell, in September 2013, in Vista, Calif., at a commercial greenhouse.

Asexual reproduction of the new cultivar 'Lilac Mist' was first performed in Vista, Calif., at a commercial greenhouse, by terminal vegetative cuttings in Fall of 2013. *Sedeveria* 'Lilac Mist' has since produced multiple generations and has shown that the unique features of this cultivar are stable and reproduced true to type.

SUMMARY OF THE INVENTION

The cultivar 'Lilac Mist' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LILAC MIST'. These characteristics in combination distinguish 'LILAC MIST' as a new and distinct *Sedeveria* x *Echeveria* cultivar:

1. 'Lilac Mist' exhibits a compact and chunky morphology that can fill 9 cm pot with single cutting.

2. 'Lilac Mist' has silver blue leaves, overlaid with a pink to violet blush, particularly in bright light.
3 'Lilac Mist' is extremely prolific when produced by leaf culture, or "leaflings", enhancing production quantities at a faster rate.
4. 'Lilac Mist', because of its subtle, attractive coloration and interesting morphology is a perfect accent for succulent groupings or dish gardens

PARENTAL COMPARISON

Plants of the new cultivar 'Lilac Mist' are similar to the seed parent in most horticultural characteristics. However, plants of the new cultivar 'Lilac Mist' differ in the following:

1. 'Lilac Mist' blushes rose to violet on apical portions of leaves, whereas 'Sed 09' does not.
2. 'Lilac Mist' produces stems that have a greater diameter than those of 'Sed 09'.
3. 'Lilac Mist' has partially flat leaves, whereas 'Sed 09' has rounded leaves.

Plants of the new cultivar 'Lilac Mist' are similar to the pollen parent, in most horticultural characteristics. However, the new cultivar 'Lilac Mist' differs the following:

1. 'Lilac Mist' has a more upright morphology than does *Echeveria* 'Lei 12'.
2. 'Lilac Mist' blushes rose to violet on the apical tips of the leaves, whereas 'Lei 12' does not.
3. *Echeveria* 'Lei 12' produces leaves with round apices, whereas 'Lilac Mist' produces leaves with sharply pointed apices.

COMMERCIAL COMPARISON

The new cultivar 'Lilac Mist' can be compared to the unpatented commercial variety *Sedum* 'Burrito'. Plants of the new variety can be commercially compared to this

*Sedum*, as they are similar in some horticultural characteristics. However, the new cultivar 'Lilac Mist' differs in the following:

1. 'Lilac Mist' expresses a rose to violet blush on the apical tips of the leaves, whereas *Sedum* 'Burrito' does not.
2. 'Lilac Mist' grows with a more upright morphology, whereas *Sedum* 'Burrito' forms stems that are more pendulous.
3. 'Lilac Mist' produces much thicker stems than does *Sedum* 'Burrito'.
4. The leaves of *Sedum* 'Burrito' are easily detached from the stem, whereas the leaves of 'Lilac Mist' are not easily detached from the stem.
5. The overall color of the foliage of *Sedum* 'Burrito' is pale blue-green, whereas the foliage of 'Lilac Mist' is silver-blue, with violet overtones.

The new cultivar 'Lilac Mist' can be compared to the unpatented commercial variety *Sedeveria* x *Echveria* 'Harry Butterfield'. Plants of this comparator are similar to plants of the new cultivar 'Lilac Mist' in most horticultural characteristics. However, the new cultivar 'Lilac Mist' differs in the following:

1. 'Lilac Mist' produces much thicker stems than 'Harry Butterfield'.
2. 'Lilac Mist' expresses a rose to violet blush on the apical tips of the leaves, whereas 'Harry Butterfield' does not.
3. 'Lilac Mist' grows with a more upright morphology, whereas 'Harry Butterfield' forms stems that are more pendulous.
4. The overall color of the foliage of 'Harry Butterfield' is blue-green, whereas the foliage of 'Lilac Mist' is silver-blue, with violet overtones.

BRIEF DESCRIPTION OF THE PHOTOGRAPHS

The accompanying photographs in FIG. 1 and FIG. 2 illustrate in full color typical plants of 'LILAC MIST' grown in a greenhouse in Vista, Calif. The photographs were taken using conventional techniques and equipment. While the colors in these photographs may display variances of color as compared to the living cultivar, due to LRV (light reflectance value), they are as accurate as possible using conventional photographic techniques. Colors in the photographs may appear to differ slightly from the color values cited in the botanical description, which accurately describe the colors of the new *Sedeveria* x *Echveria* plant. The following photographs depict plants grown under natural light conditions of 2500-4000 foot-candles. Temperatures ranged from 34° F. to 90° F. night and day. No artificial light, photoperiodic treatments or chemical treatments were given to the plants. Plants are approximately 6 months old from a vegetative cutting.

DETAILED BOTANICAL DESCRIPTION

Figure 1:
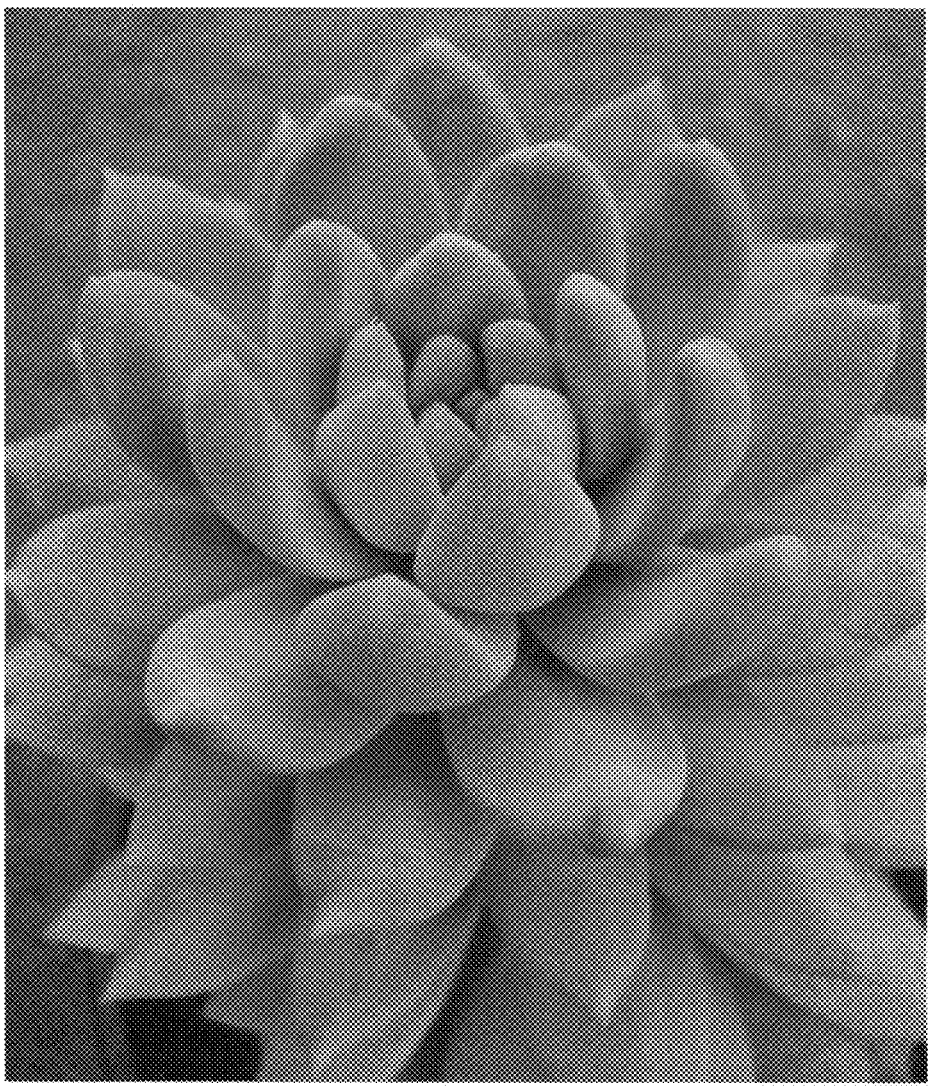
FIG. 1 illustrates in full color a typical of plant of 'Lilac Mist' with a single rosette.
Figure 2:
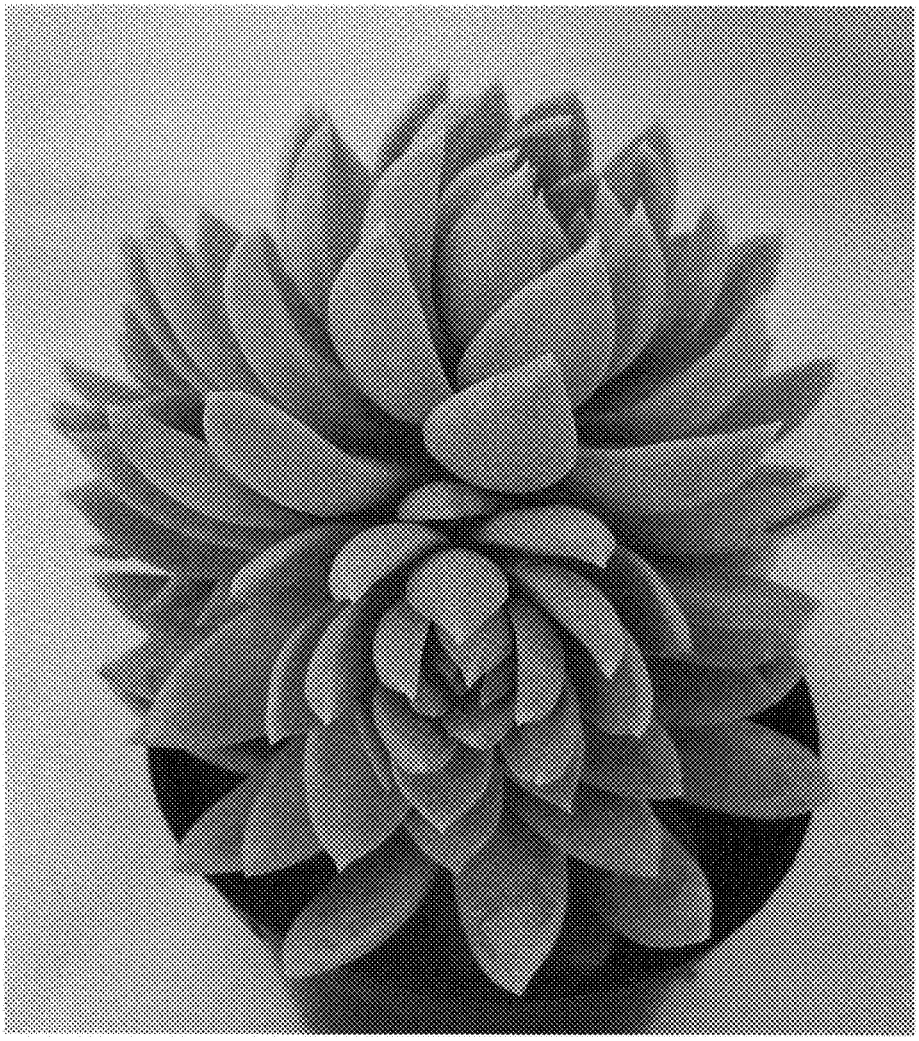
FIG. 2 illustrates in full color of plant of 'Lilac Mist' with a secondary rosette forming.

In the following description, color references are made to The Royal Horticultural Society Colour Chart, 2007, except where general terms of ordinary dictionary significance are used. The following observations and measurements describe 'Lilac Mist' plants in a commercial greenhouse in Vista, Calif. Temperatures ranged from 34° F. to 90° F. night and day. No artificial light, photoperiodic treatments or chemical treatments were given to the plants. Natural light conditions were approximately 2500-4000 foot candles of light. Measurements and numerical values represent averages of typical plant types.

Botanical classification: *Sedeveria* x *Echeveria* hybrid 'LILAC MIST'.

PROPAGATION

Type of propagation typically used: Terminal vegetative cuttings.

Time to initiate roots: About 14 days at approximately 24° C.

Root description: Fibrous.

PLANT

Age of plant described: Approximately 4 months.

Container size of the plant described: 9 cm.

Growth habit: Densely rosette plant.

Height: Approximately 10.5 cm to top of highest leaf.

Plant spread: Approximately 11 cm.

Growth rate: Rapid.

Branching characteristics: No branches, offsets occurring frequently after 3 months.

Center stem: Approximately 1.8 cm in diameter and 6 cm high. Colored near Greyed-Green 193D. Glabrous.

FOLIAGE

Leaf:

*Arrangement*.—Rosulate. Very evenly and densely arranged.

*Average length*.—Average range 3.0 cm to 5.0 cm.

*Average width*.—1.6 cm.

*Average depth*.—7 mm.

*Widest width*.—Approximately 12 cm.

*Width at base*.—1.1 cm.

*Shape of blade*.—Obovate.

*Apex*.—Cuspidate to near apiculate. Pointed structure at apex appears sharp, but, is fleshy and not sharp to the touch.

*Base*.—Truncate.

*Margin*.—Entire.

*Texture of top surface*.—Slightly glaucous.

*Texture of bottom surface*.—Slightly glaucous.

*Appearance of top surface*.—Matte.

*Appearance of top surface*.—Matte.

*Quantity of leaves per plant*.—Approximately 50 to 70 on a plant this age.

*Color*.—Young foliage upper side: Near RHS Greyed-Green 193A, center 194C. Young foliage under side: Near RHS Greyed-Green 193A, center 194C. Faintly flushed a color between Greyed-Purple N187C and 186C along upper ⅓. Mature foliage upper side: Near RHS Greyed-Green 192D, flushed over entire surface with Greyed-Purple N187C. Margins flushed 187C and 186D. Apex 193A. Base near Greyed-Green 193D, center 194C. Mature foliage under side: Near RHS Greyed-Green 192D, flushed over entire surface with Greyed-Purple N187C. Upper ⅓ flushed 187C and 186D. Apex 193A. Base near Greyed-Green 193D, center 194C.

*Venation*.—There is no visual appearance of venation.

FLOWER

Not observed to date.

REPRODUCTIVE ORGANS

Not observed to date.

OTHER CHARACTERISTICS:

Fruits and seeds: Not observed to date.

Temperature tolerance: Tolerates temperatures from approximately −2° C. to at least 35° C.

Disease/pest resistance: Neither resistance or susceptibility to normal diseases and pests of *Sedeveria* or *Echeveria* has been observed.

Drought tolerance: Tolerates at least 3 weeks of high temperatures without supplemental water, showing no serious damage to plant.

What is claimed is:

1. A new and distinct cultivar of *Sedeveria* x *Echeveria* plant named 'LILAC MIST' as herein illustrated and described.

* * * * *